US00PP15562P2

(12) United States Plant Patent
Jensen

(10) Patent No.: US PP15,562 P2
(45) Date of Patent: Feb. 15, 2005

(54) ***CAMPANULA* PLANT NAMED 'PKMH04'**

(50) Latin Name: *Campanula×haylodgensis hort*
Varietal Denomination: PKMh04

(75) Inventor: Gert Kim Jensen, Söhus (DK)

(73) Assignee: Gartneriet PKM ApS (DK)

( * ) Notice: Subject to any disclaimer, the term of this patent is extended or adjusted under 35 U.S.C. 154(b) by 0 days.

(21) Appl. No.: 10/717,649

(22) Filed: Nov. 21, 2003

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—Foley & Lardner, LLP

(57) ABSTRACT

A new and distinct cultivar of *Campanula* plant named 'PKMh04', characterized by having compact plant habit; dense and bushy plant form; vigorous growth habit and less need for chemical growth retardation; greater number of flowers per plant, and large upright blue flowers.

2 Drawing Sheets

Latin name of genus and species of the plant claimed: *Campanula×haylodgensis hort.*
Variety denomination: PKMh04.

BACKGROUND OF THE INVENTION

The present invention relates to a new and distinct cultivar of *Campanula* plant, botanically known as *Campanula× haylodgensis hort,* commonly known as Bellflower, and hereinafter referred to by the name 'PKMh04'.

The new *Campanula,* 'PKMh04', is a product of a planned mutant selection and monitoring program conducted by the Inventor, Gert K. Jensen, in Søhus, Denmark. The new *Campanula* originated from a mutation found in 2001 by the Inventor in a production batch of *Campanula× haylodgensis* 'Marion Fischer' (unpatented). The Inventor selected the new *Campanula* cultivar on the basis of its sturdy, compact, and freely flowering habit. Plants of the new *Campanula* are more upright, compact and more freely flowering than plants of 'Marion Fischer'.

Asexual reproduction of the new cultivar by terminal cuttings taken and propagated in Søhus, Denmark, has shown that the unique features of this new *Campanula* are stable and reproduce true to type in many successive generations.

SUMMARY OF THE INVENTION

Plants of the cultivar 'PKMh04' have not been observed under all possible environmental conditions. The phenotype may vary somewhat with variations in environment such as temperature, light intensity, day length, and fertility level without, however, any variance in genotype.

The following traits have been repeatedly observed and are determined to be the unique characteristics of 'PKMh04'. These characteristics in combination distinguish 'PKMh04' as a new and distinct cultivar:

1. Upright, tall plant habit;
2. Dense and bushy plant form, mainly due to more upright, stiff stems;
3. Vigorous growth habit, and less need for chemical growth retardation; and
4. Greater number of flowers per plant.

Side-by-side comparisons between the instant plant and the parental cultivar, 'Marion Fischer', were conducted by the Inventor in Stige, Denmark. Plants of 'PKMh04' differ from the cultivar 'Marion Fischer' in the following characteristics:

1. Plants of 'PKMh04' have large, white, upright, double, hose in hose, campanulate flowers.
2. Plants of 'PKMh04' have shorter internodes and petioles but larger leaves and more upright growth than plants of the cultivar 'Marion Fischer'.
3. Plants of 'PKMh04' have shorter flower peduncles than plants of the cultivar 'Marion Fischer'.
4. Plants of 'PKMh04' are taller and more compact than plants of the cultivar 'Marion Fischer'.
5. Plants of 'PKMh04' have more flowers per plants than plants of the cultivar 'Marion Fischer'.

BRIEF DESCRIPTION OF THE DRAWINGS

The accompanying photographic drawings illustrate the overall appearance of the new cultivar, showing the colors as true as it is reasonably possible to obtain in colored reproductions of this type. Colors in the photographs may differ slightly from the color values cited in the detailed botanical description, which more accurately describe the actual colors of 'PKMh04'. In the photographic drawings, the instant plant is labeled by its commercial name, 'White Wonder Great'.

The first photographic drawing shows a side perspective view of a typical flowering plant of 'PKMh04' compared with parental cultivar 'Marion Fischer' as grown in 10.5 cm pots.

The second photographic drawing shows a close-up view of typical flowering racemes of 'PKMh04' in comparison with 'Marion Fischer'.

DETAILED BOTANICAL DESCRIPTION

In the following description, color references are made to The Royal Horticultural Society (R.H.S.) Colour Chart, $4^{th}$ edition, where general terms of ordinary dictionary significance are used. Plants were grown under greenhouse conditions. The plants described were about 14 weeks old after cutting, pinched twice, but not retarded, as grown in 10.5 cm pots. For commercial production, some retardation will be required, but less retardation than parent cultivar 'Marion Fischer'.

Parentage: Mutant of *Campanula×haylodgensis* cultivar 'Marion Fischer' (unpatented).

Propagation:

*Type cutting.*—Terminal vegetative cuttings.

*Time to initiate roots.*—About 10 to 14 days at 18 to 21 C in tunnels in a greenhouse.

*Root description.*—Fine, well branched.

Plant description:

*Form.*—Perennial plant with upright plant habit. Campanulate flowers in racemes. Freely branching with lateral branches forming at every node.

*Crop time.*—After rooting, about 11 weeks are required to produce finished flowering plants in 10.5 cm pots.

*Plant height* (*soil level to top of plant plane*).—About 25 cm.

Vigor: Vigorous growth rate.

*Foliage description.*—Basal leaves single, palmate venation. Length: 32–35 mm. Width: 30–35 mm. Shape: Cordate. Apex: Acuminate. Base: Truncated. Margin: broadly dentate. Texture: smooth, glabrous. Upper leaves: Lanceolate, sessile. Length: 22 mm. Width: 7 mm. Color: Young foliage, upper and lower surfaces: RHS 137 B, green. Mature foliage, upper and lower surfaces: RHS 138 A and RHS 138 B, respectively. Venation color 138A.

Flower description:

*Flower arrangement and shape.*—Campanulate, double hose in hose flowers in racemes with small star shaped calyx. Calyx color: RHS 138 A, medium green.

*Natural flowering season.*—Continuous throughout the spring and summer. Season can be extended by vernalization and long day treatments.

*Flower longevity on the plant.*—Longevity of individual flowers is highly dependent on temperature and light conditions. Flowers persistent.

*Inflorescence size.*—Length: about 20 cm.

*Flowers.*—Upright. Length: about 14 mm. Diameter: about 25 mm. Triangular, acute petal lobes: 7 mm long and 7 mm wide. Corolla color: upper and lower surfaces, whiter than RHS 155 A.

*Peduncle.*—Strength: moderately strong. Length: about 17 mm. Diameter: about 0.5 mm. Color: RHS 138 B, light green.

Reproductive organs:

*Stamen.*—Average 2, often deformed and non-functional; RHS 2 D.

*Pistil.*—Deformed; RHS 4 D.

*Stigma.*—Deformed; RHS 4 D.

Seed: None produced.

Weather tolerance: Plants of the new *Campanula* have exhibited good tolerance to drought, rain and wind; low temperature resistant to −15C.

I claim:

1. A new and distinct cultivar of *Campanula* plant named 'PKMh04', as illustrated and described herein.

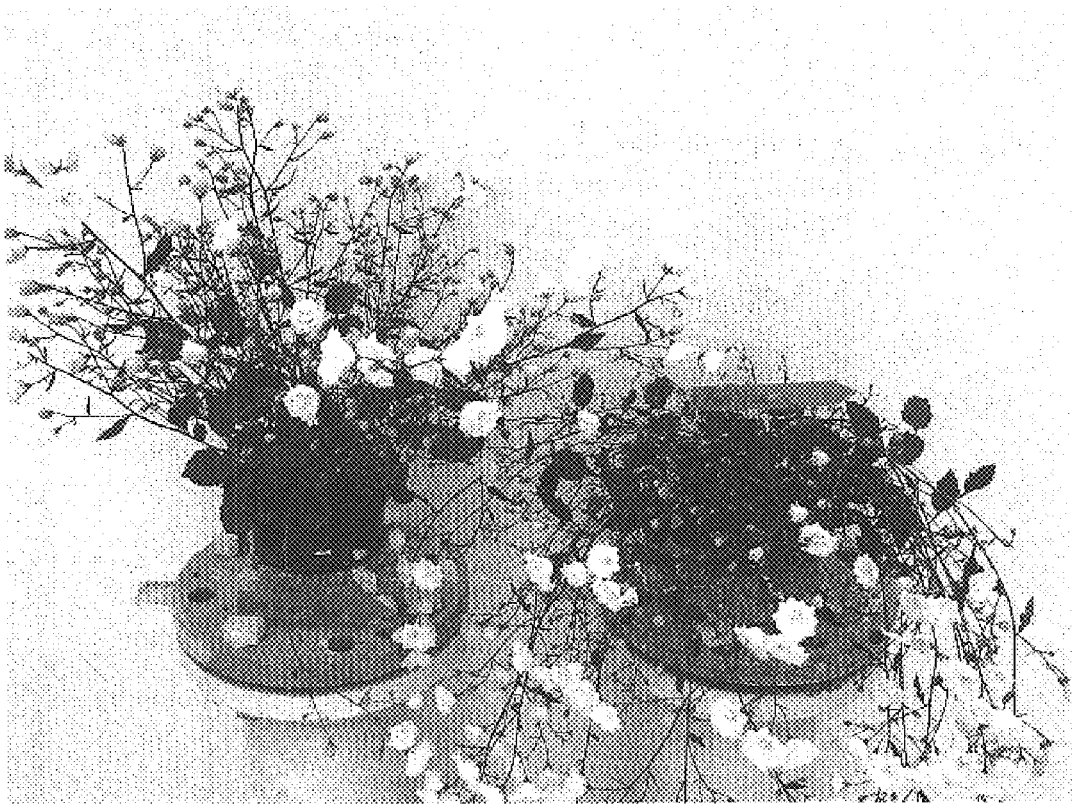

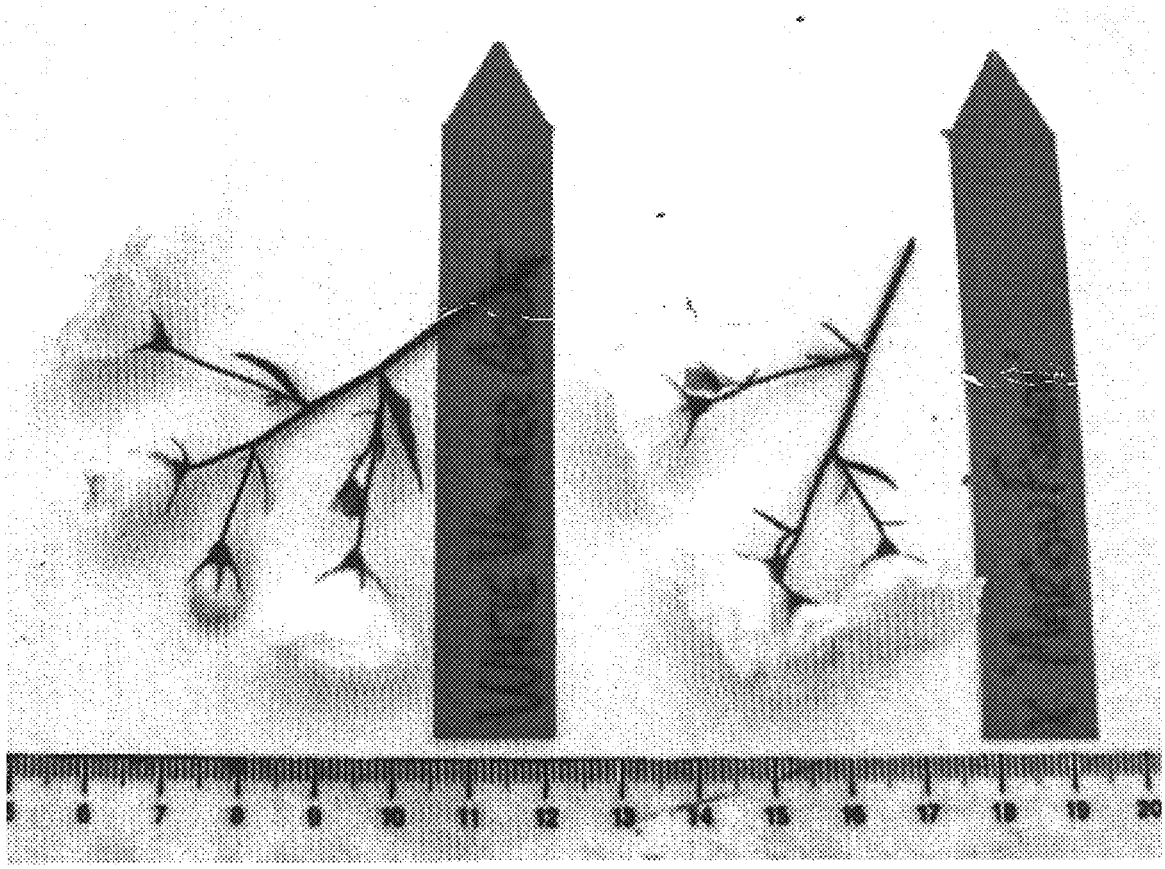

* * * * *